(12) United States Patent
Lehmann et al.

(10) Patent No.: US 6,477,226 B1
(45) Date of Patent: Nov. 5, 2002

(54) X-RAY ANALYSIS DEVICE WITH X-RAY OPTICAL SEMI-CONDUCTOR CONSTRUCTION ELEMENT

(75) Inventors: Volker Lehmann, München (DE); Rainer Golenhofen, Ettlingen (DE)

(73) Assignee: Bruker AXS Analytical X-Ray Systems GmbH, Karlsruhe (DE)

(*) Notice: Subject to any disclaimer, the term of this patent is extended or adjusted under 35 U.S.C. 154(b) by 0 days.

(21) Appl. No.: 09/441,749

(22) Filed: Nov. 17, 1999

(30) Foreign Application Priority Data

Nov. 17, 1998 (DE) .......................... 198 52 955

(51) Int. Cl.[7] .............................................. G01T 1/36
(52) U.S. Cl. .................. 378/44; 378/3; 378/6; 378/143
(58) Field of Search .................. 378/44, 3, 6, 143; 209/589; 250/306; 376/156

(56) References Cited

U.S. PATENT DOCUMENTS

| | | | |
|---|---|---|---|
| 4,933,557 A | * | 6/1990 | Perkins et al. |
| 5,416,821 A | | 5/1995 | Frazier et al. |
| 5,418,833 A | | 5/1995 | Logan |
| 6,047,044 A | * | 4/2000 | Lehmann et al. ............ 378/154 |
| 6,090,636 A | * | 7/2000 | Geusic et al. ................. 438/31 |

FOREIGN PATENT DOCUMENTS

| | | | |
|---|---|---|---|
| DE | 4327129 A1 | * | 3/1994 |
| EP | 0731472 A1 | | 9/1996 |
| WO | WO9619813 | | 6/1996 |

OTHER PUBLICATIONS

Lehmann, V.; *The Physics of Macropore Formation in Low Doped n-Type Silicon*; Oct. 1993; pp. 2836–23843.

* cited by examiner

*Primary Examiner*—David P. Porta
*Assistant Examiner*—Pamela R. Hobden
(74) *Attorney, Agent, or Firm*—Harness, Dickey & Pierce, P.L.C.

(57) ABSTRACT

An X-ray analysis device (1) having an X-ray source (2) for illuminating a sample (6) with X-radiation (4), a sample support for receiving the sample (6) and a detector (12,14) for detecting the diffracted or scattered X-radiation or fluorescent X-radiation (4') emitted by the sample, wherein an X-ray optical construction element of semi-conductor material having a plurality of channels which are essentially transparent to X-radiation (4,4') is provided in the path of rays between the X-ray source (2) and the detector (12,14), is characterized in that the X-ray optical construction element comprises a semi-conductor wafer (20;30a;30b;40;50) into which micropores (21;31;41) are etched which extend essentially in parallel in the direction of the rays and have diameters of 0.1 to 100 $\mu$m, preferably 0.5 and 20 $\mu$m. Such X-ray optical construction elements are, on the one hand, not poisonous, and on the other hand particularly transparent for X-rays, wherein a relatively high mechanical rigidity can be achieved also with large openings and very short construction lengths and thus also a particularly long service life and high pressure stability and density.

32 Claims, 2 Drawing Sheets

X-RAY ANALYSIS DEVICE WITH X-RAY OPTICAL SEMI-CONDUCTOR CONSTRUCTION ELEMENT

BACKGROUND OF THE INVENTION

The invention concerns an X-ray analysis device comprising an X-ray source for the illumination of a sample with X-rays, a sample support for receiving the sample, and a detector for detecting the diffracted or scattered X-radiation or fluorescent X-radiation emitted by the sample, wherein an X-ray optical construction element of semi-conductor material having a plurality of channels which are essentially transparent for X-rays is provided in the path of rays between the X-ray source and the detector.

An X-ray optical construction element with the above-mentioned described features is known from U.S. Pat. No. 4,933,557.

X-ray optical construction elements in the path of rays of the X-ray analysis device may be e.g. X-ray windows, X-ray collimators or X-ray lenses. The X-ray windows have to be sufficiently transparent also for soft X-radiation. For this reason, they have been produced up to now either from elements with a small z-value or having a very small thickness. Windows for X-ray tubes (e.g. for Cu-kα rays) have been produced up to now from beryllium which has the large disadvantage that such tubes have to be disposed of as special waste, since beryllium is highly poisonous. Alternatively, also X-ray windows of CVD diamond layers have been examined which are, however, relatively expensive to produce.

It is known to use thin organic films (e.g. mylar, polypropylene etc.) as window layers for X-ray detectors, however, these X-ray windows have to be additionally supported by grid plates as support to withstand the pressure of the outer atmosphere with respect to the normally evacuated X-ray detector. From U.S. Pat. No. 5,416,821 it is e.g. known to produce such grid plates of anisotropically etched 110 silicon discs having collimating properties such that the construction element is given the combined function of an X-ray collimator window.

In contrast thereto, it is the object of the present invention to present an X-ray analysis device with the above described features, wherein one or several X-ray optical construction elements are used which are, on the one hand, not poisonous, but on the other hand are particularly transparent for X-rays, whereby it is tried to achieve a relatively high mechanical rigidity also for large openings and very short construction lengths and thus a particularly long service life and high pressure stability and density.

SUMMARY OF THE INVENTION

According to the invention, this complex object is achieved in a surprisingly simple but efficient manner in that the X-ray optical construction element comprises a semi-conductor wafer having micropores extending in the direction of the rays in an essentially parallel manner and comprising diameters of between 0.1 and 100 μm, preferably 0.5 to 20 μm which are formed by etching.

An X-ray optical construction element of such a semi-conductor wafer, when used e.g. as a vacuum seal, has a considerably higher density than the films of synthetic material used up to now. In contrast to X-ray windows of beryllium, such a construction component is not poisonous and can be produced with very high mechanical rigidity e.g. by silicon nitride sheets having an extremely small thickness of 50 nm, whereas beryllium windows usually have a minimum thickness of 25 μm. Due to the refined structures, the inventive X-ray optical construction element can be produced with a very short construction length which mainly corresponds to the wafer thickness (100 to 700 μm) whereas e.g. known X-ray collimators have minimum construction thicknesses in the range of several centimeters. Of course, the small construction thickness of the inventive X-ray optical construction element is highly advantageous also with respect to its function as X-ray window or X-ray lens, wherein there is no need to make concessions to the mechanical rigidity.

The article by V. Lehmann "The Physics of Micropore Formation in Low Doped n-Type Silicon", Journal of the Electrochemical Society, Vol. 140, No. 10, 2836–2843 (1993) discloses an electro-chemical method of producing micropores in semi-conductor wafers. The holes referred to as "macropores" in said article having diameters of a magnitude of 10 μm are etched in such a manner that the walls between the generated pores are very thin (e.g. 2 μm) and that each respective pore tip is closed by a likewise thin layer (in general only a few μm) of silicon.

In a preferred embodiment of the inventive X-ray analysis device, the micropores of the X-ray optical construction element have not been etched continuously such that a ground surface having a thickness of between 1 to 100 μm, preferably between 5 and 20 μm remains. For this reason, the effective silicon layer for the penetrating X-ray light is very thin, which makes the X-ray optical construction component highly transparent. The grid of the pore walls, however, provides for a relatively high mechanical stability despite the apparently small wall thickness.

In a preferred further development of this embodiment, the inner side of the micropores is lined with a stabilizing layer which closes the micropores on one side of the semi-conductor wafer. This enhances the mechanical stability of the X-ray optical construction element without considerably impairing the transparency for X-radiation.

In order to further increase the X-ray transparency, in a particularly preferred further development, the ground surface of the semi-conductor wafer on the side on which the stabilizing layer closes the pores is etched down to the stabilizing layer. This selective etching of the wafer material leaves only a thin film of approximately 20 to 100 nm thickness of the stabilizing layer which covers the pore ground and thus generates an extremely thin window for the X-radiation. In the ideal case, the inventive X-ray optical construction element used as a window for X-ray fluorescence detectors may be transparent for energies of not more than around 100 eV.

In a particularly preferred manner, the stabilizing layer is disposed by means of CVD methods (chemical vapor deposition). CVD methods of this type are known per se. The layered material is thereby disposed onto the surface to be covered and, after cooling down, is subjected to compression thereby avoiding the formation of cracks.

It is preferred to use silicon nitride ($Si_3N_4$), boron nitride (BN), boron hydride (BH) or possibly also boron carbide or silicon carbide or even carbon as materials for the stabilizing layer. With these it is possible to produce extremely thin films which cover the ground of the pore, but still have sufficiently high mechanical rigidity and vacuum density when the inventive X-ray optical construction element is used as X-ray window.

One embodiment of the inventive X-ray analysis device is particularly preferred in which the semi-conductor wafer of the X-ray optical construction element consists of silicon. A varied and common technology for the micro-fine processing of this material is known from the production of electronic components.

The semi-conductor wafer according to the inventive X-ray optical construction element will have in general a thickness of between 10 μm and 1 mm, preferably between 100 and 700 μm.

It is the easiest to produce micropores having a circular cross-section with the processing methods known per se from semi-conductor technology. With modifications of the known methods, it is also possible to produce other cross-sectional shapes, e.g. elliptical cross-sections.

In the easiest case, the micropores may comprise a cross-section which is constant along the pore length. This geometrical shape will be sufficient for most cases of application.

When the inventive X-ray optical construction element is used e.g. as X-ray lens, it may be advantageous to provide the micropores with a cross-section that varies along the pore length.

One embodiment is particularly simple in which the micropore axis extends essentially perpendicularly to the surface of the semi-conductor wafer.

As an alternative, embodiments are also feasible, where in the micropore axis extends in an inclined manner to the surface of the semi-conductor wafer.

In a further alternative, the micropores are curved in their direction of passage. This requires, however, considerable more effort in production as compared with the two above described embodiments, but at the same time opens a wide field of different applications of the X-ray optical construction element according to the invention.

Thus, in a preferred further development it is possible to produce an X-ray lens which is considerably flatter in the direction of passage of the X-radiation than all hitherto known X-ray optical construction elements of this type.

In other preferred embodiments, the X-ray optical construction element has the function of an X-ray collimator which can be designed with a particularly short length due to the inventive construction of the construction element in the direction of passage of radiation.

In further particularly preferred embodiments, the X-ray optical construction element is used as an X-ray window in the X-ray analysis device. In this case, the extremely small minimum thickness of the inventive X-ray optical construction element and its very high mechanical strength are of particular advantage also with large openings and its high density is of particular advantage as vacuum seal.

One further development of the above-mentioned embodiments is particularly preferred in which the X-ray optical construction element is positioned directly in front of the X-ray detector and fulfills the combined function of a collimator window.

In this connection, it is particularly advantageous if the X-ray optical construction element forms a construction unit with the X-ray detector.

In its function as X-ray window or combined collimator window, the X-ray optical construction element may form a construction unit with the X-ray source in further embodiments.

The embodiments described above may be used also together in an X-ray analysis device according to the invention.

A preferred embodiment utilizes the particularly high rigidity properties of the X-ray optical construction element according to the invention, in which the path of rays extends partly through an evacuated space which is separated from a non-evacuated space by the X-ray optical construction element.

A further particularly preferred embodiment provides that several micropores of the X-ray optical construction element are connected in each case to form microslots through etching of the wafer material between the pores. In this manner, collimation and/or focussing of the X-radiation in a selected direction can be carried out and a better transmission through the X-ray optical construction element is achieved.

An X-ray optical construction element for the use in an X-ray analysis device of the above-mentioned kind is also within the scope of the invention, wherein the X-ray optical construction element is produced according to the following method:

(a) Application of etched cores onto the front side of a semi-conductor wafer at the locations provided for the etching of micropores by means of alkaline etching according to a lithographic standard method;

(b) Etching of the micropores from the front side of the semi-conductor wafer by means of aqueous hydrofluoric acid (HF) through application of an electric potential in the range of several Volts, wherein the etching flow is generated preferably by illumination of the rear side of the semi-conductor wafer;

(c) Coating the semi-conductor wafer by means of the CVD method, preferably with $Si_3N_4$;

(d) Etching of the rear side of the semi-conductor wafer down to the CVD layer in the tips of the micropores.

Finally, in further advantageous embodiments the following additional step may follow:

(e) Removing of the CVD layer, preferably by means of hydrofluoric acid.

The coating which served as mechanical support during the production of the X-ray optical construction element is e.g. no longer absolutely necessary for the function of the component as collimator such that its removal results in a particularly high transparency for the X-radiation. However, the mechanical stability is then no longer sufficient to be used as X-ray window with pressures of relatively high differences.

Further advantages of the invention can be gathered from the description and the drawing. The features mentioned above and below may be used in accordance with the invention either individually or collectively in any arbitrary combination. The embodiments shown and described are not to be understood as exhaustive enumeration but rather have exemplary character for describing the invention.

The invention is shown in the drawing and is explained in more detail by means of embodiments. In the drawing:

DESCRIPTION OF THE PREFERRED EMBODIMENT

Figure 1:
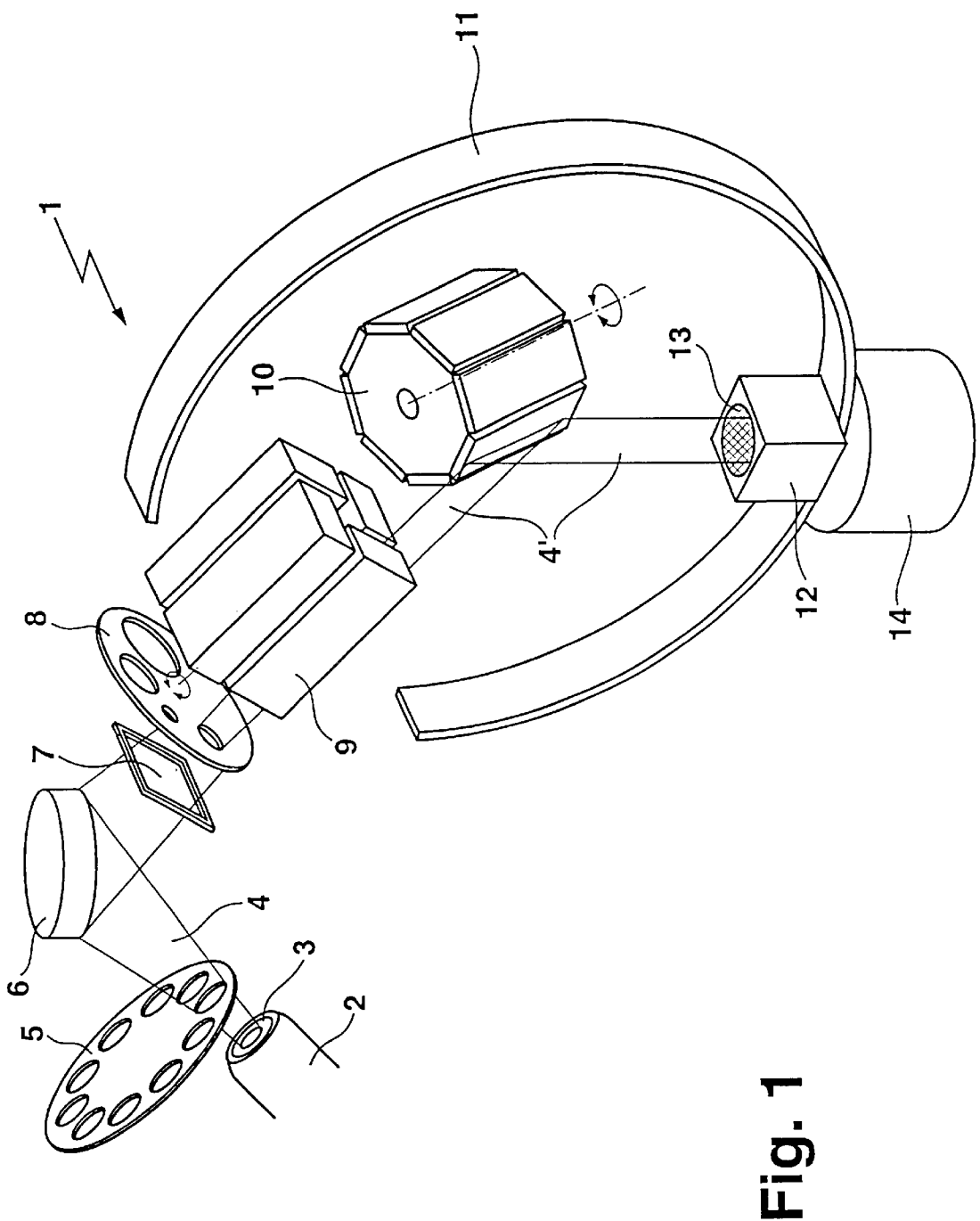
FIG. 1 shows a schematic spatial view of the components of an embodiment of the inventive X-ray analysis device.

FIG. 1 shows schematically the components of an X-ray analysis device 1 in their spatial relation. In an X-ray source 2 having an X-ray window 3, X-radiation 4 is generated which passes via an X-ray filter arrangement 5 to a sample 6, from which diffracted or scattered X-radiation or fluorescent X-radiation 4' passes through a window 7 which, in case of liquid samples, separates the sample space which is flooded with gas, from the evacuated spectrometer space, and can reach via a collimator diaphragm 8 matched with the size of the sample, an X-ray collimator 9 formed of four individual collimators in the embodiment shown in FIG. 1, which may enter the path of the X-radiation 4' emitted by the sample 6, as required, through rotation of the collimator device 9.

The X-radiation 4' emitted by the X-ray collimator 9 is diffracted at an analysis unit 10 which, in the embodiment shown, consists of eight different analyzing crystals distributed around the periphery of a rotatable drum. From there, the X-radiation 4' passes via a collimator with entering window 13 into an X-ray detector mounted on a goniometer 11 which consists of a proportional counter 12 and a scintillation counter 14.

The X-ray analysis device 1 in its function as X-ray window, X-ray collimator, combined collimator window or e.g. also X-ray lens, comprises at least one X-ray optical construction element which comprises a semi-conductor wafer into which a plurality of parallel micropores having diameters of between 0.1 and 100 $\mu$m are etched which extend in the direction of the X-radiation 4, 4'. The semi-conductor wafer will generally consist of silicon and have a thickness of between 10 $\mu$m and 1 mm, preferably between 100 and 700 $\mu$m.

The geometrical shape of the micropores in the semi-conductor wafer of the respective X-ray optical construction element may be varied depending on the function and use. The X-ray optical construction element according to the invention may also form a construction unit with other construction elements of the X-ray analysis device 1, e.g. an X-ray detector like e.g. the proportional counter 12 or, in its function as X-ray window 3, may form a unit with the X-ray tube 2.

The basic construction of the X-ray optical construction element is shown in FIGS. 2 to 5.

Figure 2:
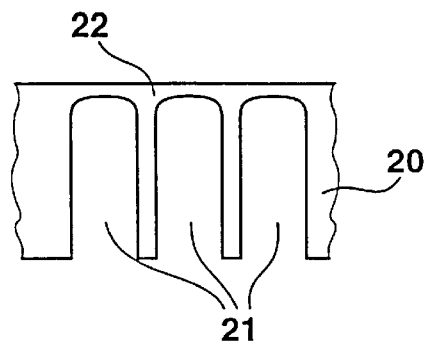
FIG. 2 shows a schematic section through the semi-conductor wafer of an embodiment of the X-ray optical construction element.

FIG. 2 shows a section through a semi-conductor wafer 20 with the above-described etched micropores 21. Since the etching of the micropores 21 is not continuous in the semi-conductor wafer 20, there remains a stabilizing ground surface 22 of a thickness in the range of approximately 5 to 20 $\mu$m. The parallel micropores 21 may assume e.g. a collimation function for the X-radiation 4, 4'.

Figure 3A:
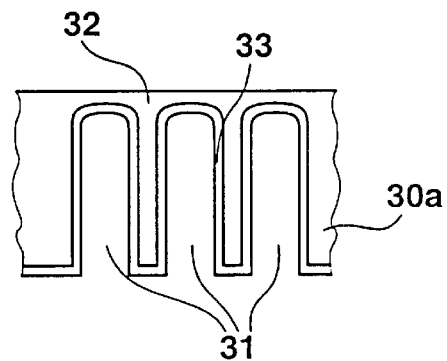
FIG. 3a corresponds to FIG. 2, wherein, however, the stabilizing layer is provided on the inner side of the micropores of the semi-conductor wafer.

In order to increase the stability of the X-ray optical construction element, the micropores 31 of the semi-conductor wafer 30a, shown in FIG. 3a, may be lined with a stabilizing layer 33 which closes the micropores 31 on the side of the semi-conductor wafer 30a supporting the ground surface 32. The stabilizing layer 33 may be disposed e.g. by means of a CVD method (=chemical vapor deposition). Silicon nitride, silicon carbide, boron nitride, boron hydride, boron carbide and/or carbon are suitable materials for the stabilizing layer 33.

Figure 3B:
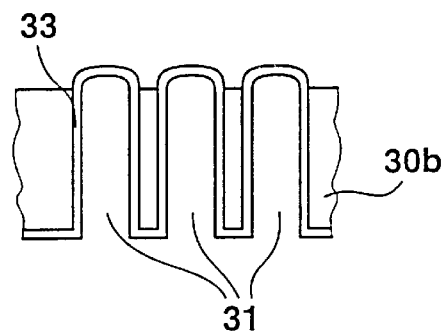
FIG. 3b corresponds to FIG. 3a, wherein, however, the ground surface of the semi-conductor wafer is etched down to the stabilizing layer.

As shown in FIG. 3b, the ground surface 32 that remained in FIG. 3a, can be etched such that the ends of the pores 31 are merely closed to the one side by the stabilizing layer 33. The semi-conductor wafer 30b itself comprises in this case continuous micropores 31.

Figure 4:
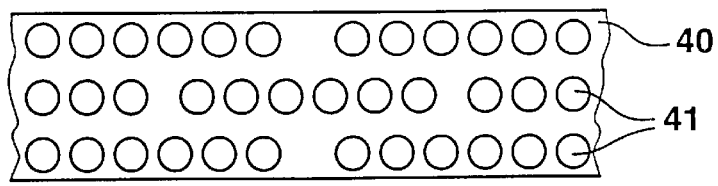
FIG. 4 shows a schematic plan view of the micropores of a semi-conductor wafer.

FIG. 4 shows a plan view of a semi-conductor wafer 40 with etched micropores 41. The micropores 41 comprise, in this embodiment, a circular cross-section and extend approximately perpendicularly to the surface of the semi-conductor wafer 40. In general, the micropores 21, 31, 41 will comprise a cross-section which is constant along the pore length, as shown in FIGS. 2 to 3b.

In further embodiments of the X-ray optical construction element, which are not shown in the drawing, the micropores may also have any cross-sectional shape other than circular, which may vary along the length of the pore. The micropore axis may also extend in an inclined manner with respect to the surface of the respective semi-conductor wafer or the micropores may be curved in their direction of passage. The latter case would e.g. be advantageous if the corresponding X-ray optical construction element were to be used as X-ray lens.

Figure 5:
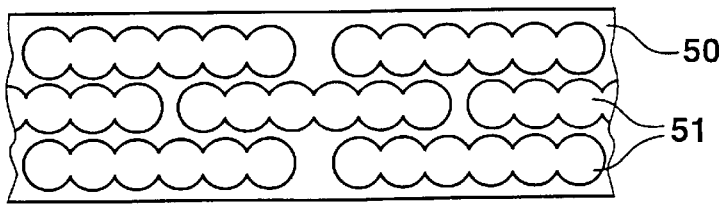
FIG. 5 corresponds to FIG. 4, wherein, however, the micropores are united to form slots.

A further particular embodiment is shown in FIG. 5, wherein several micropores of the semi-conductor wafer 50 are connected in each case through etching of the wafer material therebetween to form microslots 51. In this manner, collimation can be carried out preferably in a direction transverse to the path of rays, whereas there will be no collimation in the other direction that corresponds with the longitudinal extension of the slots 51.

The following table shows an assessment of transmission of X-radiation 4, 4' in percentage values without taking into consideration a supporting grid and without the ground surfaces 22, 32, wherein on the one hand the coating material was boron nitride, and on the other hand silicon nitride. The last column shows the transmission values for a mylar foil as comparison:

| Element | Kα (eV) | 50 nm BN 1.9 g/cm$^3$ | 50 nm Si$_3$N$_4$ 3.1 g/cm$^3$ | 1000 nm (Mylar foil) 1.0 g/cm$^3$ |
|---|---|---|---|---|
| Be | 108.5 | 79% | 28% | 14.7% |
| B | 183.3 | 93% | 42% | 53% |
| C | 277 | 84% | 69% | 79% |
| N | 392.4 | 93% | 85% | 8% |
| O | 524.9 | 88% | 83% | 29% |

This evaluation shows that the X-ray windows according to the invention do not exhibit the considerable disadvantages inherent in windows of synthetic material like e.g. low transmission of nitrogen radiation.

The mechanical rigidity of the films of coating material 33 that remain after etching of the ground surface 32 at the tips of the micropores 31 can be assessed through the maximum difference in pressure p max which the arrangement can withstand:

$p \text{ max} = 1.5 \, (d/r)^2 \text{sigma}$ d=50 nm, r=1000 nm and sigma=1.4 10$^{11}$ dyne/cm$^2$ results in p max=518 atm.

With all vague factors (sigma was used for the Si$_3$N$_4$ monocrystal, the formula holds for plane plates), this shows clearly that even considerably thinner coatings can safely withstand a pressure of one atmosphere in their function as X-ray window.

The above was confirmed by experiments concerning the mechanical loading capacity and optimization of the supporting grids produced by anisotropic etching.

What is claimed is:

1. X-ray analysis device (1) comprising an X-ray source (2) for illuminating a (6) sample with X-radiation (4), a sample support for receiving the sample (6) and a detector (12, 14) for verifying diffracted or scattered X-radiation or fluorescent X-radiation (4') emitted by the sample (6), wherein in the path of rays, between the X-ray source (2) and the detector (12, 14) there is provided an X-ray optical construction element of semi-conductor material having a plurality of channels which are essentially transparent to X-radiation (4, 4'), characterized in that the X-ray optical construction element comprises a semi-conductor wafer (20; 30a; 30b; 40; 50) with micropores (21; 31; 41) etched therein and extending essentially in parallel in the direction of the rays and having diameters of between 0.1 and 100 $\mu$m.

2. X-ray analysis device according to claim 1, characterized in that the micropores (21; 31; 41) are etched in a discontinuous manner leaving a ground surface (22; 32) having a thickness in the range of between 1 and 100 $\mu$m.

3. X-ray analysis device according to claim 2, characterized in that the inside of the micropores (31) is lined with a stabilizing layer (33) which closes the micropores (31) on one side of the semi-conductor wafer (30a;30b).

4. X-ray analysis device according to claim 3, characterized in that the ground surface (32) of the semi-conductor wafer (30b) on the side where the stabilizing layer (33) closes the micropores (31) has been etched down to the stabilizing layer (33).

5. X-ray analysis device according to claim 3 or 4, characterized in that the stabilizing layer (33) has been disposed by means of a CVD method (=chemical vapor deposition).

6. X-ray analysis device according to claim 5 characterized in that the stabilizing layer (33) comprises silicon nitride, silicon carbide, boron nitride, boron hydride, boron carbide and/or carbon.

7. X-ray analysis device according to claim 1, characterized in that the micropores have a variable cross-section along the pore length.

8. X-ray analysis device according to claim 7, characterized in that the micropores are curbed in their direction of passage.

9. X-ray analysis device according to claim 8, characterized in that the X-ray optical construction element has the function of an X-ray lens.

10. X-ray analysis device according to claim 1, characterized in that the X-ray optical construction element has the function of a collimator (9, 13).

11. X-ray analysis device according to claim 1, characterized in that the X-ray optical construction element has the function of an X-ray window (3, 7, 13).

12. X-ray analysis device according claim 11, characterized in that the X-ray optical construction element (13) is positioned directly in front of the detector (12) and has the combined function of a collimator window.

13. X-ray analysis device according to claim 12, characterized in that the X-ray optical construction element (13) forms a construction unit with the detector (12).

14. X-ray analysis device according to claim 11, characterized in that the X-ray optical construction element (3) forms a construction unit with the X-ray source (2).

15. X-ray analysis device according to one of claims 1 to 4, characterized in that the path of rays (4, 4') extends partly through an evacuated space which is separated from a non-evacuated space by the X-ray optical construction element (7).

16. X-ray analysis device according to one of claims 1 to 4, characterized in that several micropores of the X-ray optical construction element are connected in each case by etching the wafer material located inbetween to form microslots (51).

17. X-ray analysis device according to claim 1, characterized in that the micropore axis extends essentially perpendicularly to the surface of the semi-conductor wafer (20;30a;30b;40;50).

18. X-ray analysis device according to claim 1, characterized in that the micropore axis extends in an inclined manner with respect to the surface of the semi-conductor wafer.

19. X-ray analysis device according to claim 1, characterized in that the micropores are curved in their direction of passage.

20. X-ray analysis device according to claim 7, characterized in that the X-ray optical construction element has the function of an X-ray lens.

21. X-ray analysis device according to claim 1, characterized in that the X-ray optical construction element has the function of a collimator (9,13).

22. X-ray analysis device according to claim 1, characterized in that the X-ray optical construction element has the function of an X-ray window (3,7,13).

23. X-ray analysis device according to claim 19, characterized in that the X-ray optical construction element (13) is positioned directly in front of the detector (12) and has the combined function of a collimator window.

24. X-ray analysis device according to claim 9, characterized in that the X-ray optical construction element (13) forms a construction unit with the detector (12).

25. X-ray analysis device according to claim 8, characterized in that the X-ray optical construction element (3) forms a construction unit with the X-ray source (2).

26. X-ray analysis device according to claim 1, characterized in that several micropores of the X-ray optical construction element are connected in each case by etching the wafer material located inbetween to form microslots (51).

27. X-ray optical construction element for the use in an X-ray analysis device (1) according to claim 1, characterized in that the X-ray optical construction element is constructed according to the following method:
   (a) Application of etched cores on the front side of a semi-conductor wafer (20;30a;30b;40;50) at the locations provided for etching the micropores (21;31;41) by means of alkaline etching according to a lithographical standard method;
   (b) Etching of the micropores (21;31;41) on the front side of the semi-conductor wafer (20;30a;30b;40;50) by means of aqueous hydrofluoric acid (HF) through application of an electric potential in the range of a few Volts, wherein the etching current is generated preferably through illumination of the rear side of the semi-conductor wafer (20;30a;30b;40;50);
   (c) Coating of the semi-conductor wafer (30a;30b) by means of the CVD method, preferably with $Si_3N_4$;
   (d) Etching of the rear side of the semi-conductor wafer (30b) down to the CVD layer (33) in the tips of the micropores (31).

28. X-ray optical construction element according to claim 13, characterized in that the X-ray optical construction element has been produced through the following additional step:
   (e) removing of the CVD layer (33), preferably by means of hydrofluoric acid.

29. X-ray analysis device according to claim 7, characterized in that the path of rays (4, 4') extends partly through an evacuated space which is separated from a non-evacuated space by the X-ray optical construction element (7).

30. X-ray analysis device of claim 7, characterized in that several micropores of the X-ray optical construction element are connected in each case by etching the wafer material located inbetween to form microslots (51).

31. X-ray optical construction element for the use in an X-ray analysis device (1) according to claim 7, characterized in that the X-ray optical construction element is constructed according to the following method:
   a. Application of etched cores on the front side of a semi-conductor wafer (20; 30a; 30b; 40; 50) at the locations provided for etching the micropores (21; 31; 41) by means of alkaline etching according to a lithographical standard method;
   b. Etching of the micropores (21; 31; 41) on the front side of the semi-conductor wafer (20; 30a; 30b; 40; 50) by means of aqueous hydrofluoric acid (HF) through application of an electric potential in the range of a few Volts, wherein the etching current is generated preferably through illumination of the rear side of the semi-conductor wafer (20; 30a; 30b; 40; 50);
   c. Coating of the semi-conductor wafer (30a; 30b) by means of the CVD method, preferably with $Si_3N_4$;
   d. Etching of the rear side of the semi-conductor wafer (30b) down to the CVD layer (33) in the tips of the micropores (31).

32. X-ray optical construction element according to claim 31, characterized in that the X-ray optical construction element has been produced through the following additional step:
   e. removing of the CVD layer (33), preferably by means of hydrofluoric acid case by etching the wafer material located inbetween to form microslots (51).

* * * * *

UNITED STATES PATENT AND TRADEMARK OFFICE
CERTIFICATE OF CORRECTION

PATENT NO. : 6,477,226 B1
DATED : November 5, 2002
INVENTOR(S) : Volker Lehmann et al.

It is certified that error appears in the above-identified patent and that said Letters Patent is hereby corrected as shown below:

Column 7,
Line 53, after "according" insert -- to --.

Column 10,
Lines 17-18, delete "case by etching the wafer material located inbetween to form microslots (51)".

Signed and Sealed this

Tenth Day of February, 2004

JON W. DUDAS
*Acting Director of the United States Patent and Trademark Office*